United States Patent
Franzmann et al.

(10) Patent No.: US 8,088,591 B2
(45) Date of Patent: Jan. 3, 2012

(54) BIOMARKERS FOR DETECTION AND DIAGNOSIS OF HEAD AND NECK SQUAMOUS CELL CARCINOMA

(75) Inventors: Elizabeth J. Franzmann, Miami, FL (US); Vinata B. Lokeshwar, Miami, FL (US)

(73) Assignee: University of Miami, Miami, FL (US)

( * ) Notice: Subject to any disclaimer, the term of this patent is extended or adjusted under 35 U.S.C. 154(b) by 186 days.

(21) Appl. No.: 12/300,523

(22) PCT Filed: May 14, 2007

(86) PCT No.: PCT/US2007/011511
§ 371 (c)(1),
(2), (4) Date: Feb. 20, 2009

(87) PCT Pub. No.: WO2007/133725
PCT Pub. Date: Nov. 22, 2007

(65) Prior Publication Data
US 2009/0325201 A1 Dec. 31, 2009

Related U.S. Application Data

(60) Provisional application No. 60/799,925, filed on May 12, 2006.

(51) Int. Cl.
*G01N 33/574* (2006.01)

(52) U.S. Cl. .......................................... 435/7.23; 435/7.1
(58) Field of Classification Search .................. None
See application file for complete search history.

(56) References Cited

U.S. PATENT DOCUMENTS

2005/0008646 A1* 1/2005 Young et al. ............... 424/155.1
2005/0214880 A1 9/2005 Franzmann et al.

OTHER PUBLICATIONS

Franzmann et al, Int J Cancer, 2003, 106:438-445.*
Tockman et al, Cancer Res., 1992, 52:2711s-2718s.*
Franzmann et al, Cancer Epidemiol Biomarkers Prev, Mar. 2005, 14:735-9.*
Notification of Transmittal of the International Search Report and The Written Opinion of the International Searching Authority Form PCT/ISA/200.
International Search Report Form PCT/ISA/210.
The Written Opinion Form PCT/ISA/237.

* cited by examiner

*Primary Examiner* — Misook Yu
*Assistant Examiner* — Mark Halvorson
(74) *Attorney, Agent, or Firm* — Novak Druce + Quigg LLP

(57) ABSTRACT

Novel, sensitive and specific markers and methods for diagnostics and monitoring of head and neck squamous cell carcinoma (HNSCC) are provided. Kits and methods for the use of hyaluronic acid, hyaluronidase and CD44 to diagnose HNSCC are described.

23 Claims, 7 Drawing Sheets

BIOMARKERS FOR DETECTION AND DIAGNOSIS OF HEAD AND NECK SQUAMOUS CELL CARCINOMA

FIELD OF INVENTION

The invention relates to a panel of biomarkers and methods for diagnosis of head and neck squamous cell carcinoma (HNSCC). In particular, sensitive, specific and reliable detection and identification of biomarkers that are uniquely produced in head and neck squamous cell carcinoma (HNSCC) are provided.

BACKGROUND

Head and neck squamous cell carcinoma (HNSCC) accounts for almost 90% of cancers involving the upper aerodigestive tract (UADT). In the United States in 2005, cancers of the oral cavity, pharynx and larynx are expected to account for nearly 3% of incident cancers and 2% of cancer deaths. There are approximately 500,000 new cases diagnosed world-wide each year. Men are affected over two times more than women. Over half of these cancers involve the oral cavity. The rest are divided equally between larynx and pharynx.

There is no effective early detection program for head and neck squamous cell carcinoma (HNSCC). A recent study from India shows a survival advantage for screening by oral cavity exam. However sensitivity and specificity of this method are only 75%. Screening by physical exam is expensive, skill-dependent, and cannot detect occult disease. Poor detection practices likely contribute to the poor survival noted in black males and patients from low SES. Access to skilled practitioners may pose a challenge to individuals with limited material resources.

Five-year survival rates for HNSCC are low and have not improved in several decades. Moreover, patients with this disease experience severe morbidity including disfigurement, speech, swallowing and breathing problems. Late stage of diagnosis and propensity to recur are challenges that thwart efforts to improve outcomes in these patients. These challenges are more pronounced in black patients compared to white patients and economically disadvantaged populations compared to wealthy populations. Effective early detection programs that are targeted to high-risk populations may result in diagnosis of a higher proportion of patients with early stage disease and therefore better outcomes.

There is thus an urgent need in the art to develop tests for the early diagnosis of these types of tumors.

SUMMARY

A panel of biomarkers for the detection/diagnosis of head and neck squamous cell carcinoma (HNSCC) are described. CD44, hyaluronic acid (HA) and hyaluronidase (HAase) comprise a related group of molecules with distinct roles in tumorigenesis that are detectable in saliva, and have been found to be useful for early detection of HNSCC. In particular, the panel of biomarkers are useful for distinguishing between patients with benign conditions and those with malignant disease.

Thus, the above-mentioned biomarkers can be considered indicators of the presence of HNSCC or increased risk thereof in a subject.

Accordingly, it is one object to provide a method of detecting/diagnosing HNSCC in a subject, the method comprising assaying for the presence of at least one biomarker in a subject sample, and correlating a detection of the biomarker(s) with a diagnosis of, or indication of increased risk of, developing HNSCC, wherein the correlation takes into account the detection of one or more biomarker in the subject sample, as compared to the frequency or level of occurrence of the biomarker(s) in normal subjects, wherein the biomarker(s) is selected from: hyaluronic acid (HA); hyaluronidase (HAase) and CD44. For a diagnosis of HNSCC or increased risk thereof, at least one of the biomarkers is detected, more preferably, a plurality of the biomarkers are detected.

In one embodiment, the method of detecting HNSCC comprises comparing hyaluronic acid; hyaluronidase, CD44 and/or total protein values obtained from a patient with values from normal subjects. Total protein values in the saliva of patients with HNSCC have been found to be higher than total protein values in normal subjects.

Thus, in one particular embodiment, increased CD44, HA, and HAase levels in saliva or an oral rinse with normalization to protein values are diagnostic of HNSCC, or increased risk of future development thereof. In another particular embodiment, increased absolute levels of CD44, HA, and HAase in saliva or an oral rinse (without normalization to protein values) are diagnostic of HNSCC, or increased risk of future development thereof. In yet another embodiment, increased values of protein in saliva or an oral rinse are diagnostic of HNSCC, or increased risk of future development thereof.

Levels of HA, HAase, CD44, and/or total protein are also indicative of tumor stage. For example, low levels of elevation are indicative of early stage cancer; higher levels are indicative of later stage cancer. In one embodiment, detection of at least one biomarker is diagnostic of tumor stage.

The type of biomarker detected can also be indicative of tumor stage.

In yet another embodiment, a method of monitoring effectiveness of treatment of HNSCC is provided, comprising measuring at least one of: HA; HAase, CD44, and/or total protein in a biological sample obtained from a patient, wherein decreased levels of at least one of HA; HAase, CD44, and/or total protein compared to levels detected prior to treatment in the same patient, is indicative of effective treatment.

In a further embodiment, a method of predicting the course of HNSCC in a subject is provided, comprising measuring at least one of HA, HAase, CD44 and/or total protein in a biological sample obtained from said subject, wherein the degree of elevation of HA, hyaluronidase, CD44, and/or total protein compared to normal subjects, or in a population of subjects with HNSCC, is indicative of the severity of HNSCC, with a greater degree of elevation being indicative of more severe disease, and/or a less favorable prognosis. It is noted that in the case of CD44 very low levels may also be indicative of poorer prognosis since in very severe cases some genes including CD44 get turned off by promoter hypermethylation.

In another embodiment, a method of predicting recurrence of HNSCC in a subject is provided, comprising measuring at least one of HA, HAase, CD44, and/or total protein in a biological sample obtained from said subject, wherein an elevated level of HA, HAase, CD44, and/or total protein compared to normal subjects is predictive of increased likelihood of recurrence (i.e. of the same or an additional new tumor) of HNSCC. The presence or level of the biomarker(s) can be compared with prior values obtained from the subject (e.g. following treatment)

The biomarkers can be detected, for example, using a protein assay, binding assay or an immunoassay. Exemplary assays are described in detail in the examples which follow.

For a positive diagnosis, the biomarkers and/or total protein detected are elevated as compared to values in normal healthy controls.

The subject sample may be selected, for example, from the group consisting of oral rinse, saliva, blood, blood plasma, serum, urine, tissue, cells, and liver. Preferably, the sample is an oral rinse.

In yet another embodiment, a kit for diagnosing/detecting HNSCC or elevated risk thereof in a subject is provided. The kit may also be used for measuring treatment success or predicting recurrence of HNSCC.

In one form, the kit comprises at least one means of detecting a biomarker selected from the group consisting of HA, HAase and total protein. Preferably the kit comprises means for detecting HA, HAase and total protein. The kit may also contain means for detecting CD44, in particular solCD44. The kit may contain one or more of: a substrate or container for holding a biological sample (e.g. of saliva or an oral rinse), reference standard(s) of biomarker(s) in solution or solid form, one or more antibodies specific for the biomarkers, and directions for carrying out detection assay(s) for the biomarkers with the contents of the kit.

In one preferred embodiment, the kit comprises means for detecting HA, HAase, solCD44 and total protein.

In one specific embodiment, the kit comprises: (a) a substrate or container for holding a biological sample isolated from a human subject suspected of having HNSCC, or of being at risk thereof; (b) a fluorogenic agent that detects at least one biomarker; (c) a panel of biomarkers; and optionally, (d) printed instructions for reacting the agent with the biological sample or a portion of the biological sample to detect the presence or amount of at least one biomarker in the biological sample. Preferably, the kit comprises a panel of biomarkers of any one or more of: HA and hyaluronidase to be used as standards, along with means of detecting HA and HAase and total protein. The kit may also contain a standard for and/or means for detecting CD44, in particular solCD44. Optionally, the kit comprises antibodies specific for any one or more of biomarkers: HA, HAase, and CD44.

Other aspects are described infra.

BRIEF DESCRIPTION OF THE DRAWINGS

The invention is pointed out with particularity in the appended claims. The above and further advantages of this invention may be better understood by referring to the following description taken in conjunction with the accompanying drawings, in which:

DETAILED DESCRIPTION

Figure 1:
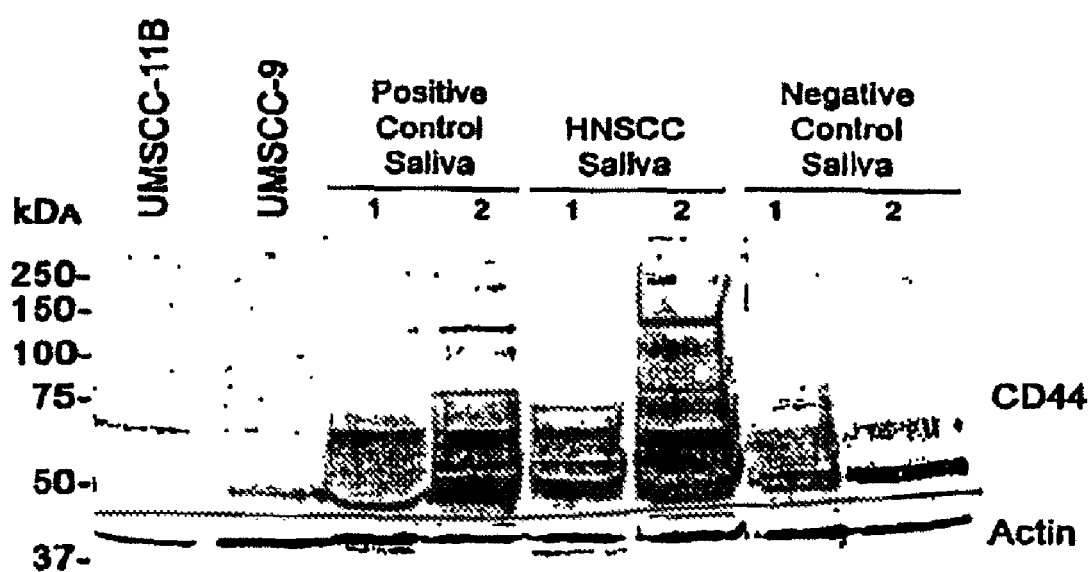
FIG. 1 is a scan of a Western blot comparing CM of HNSCC cell lines, SolCD44 positive control saliva, HNSCC saliva, and solCD44 negative control saliva.

HNSCC includes cancers involving the oral cavity, pharynx, and larynx. Primary treatment modalities entail combinations of surgery, radiation, and chemotherapy. Because these tumors are often diagnosed in late stage, the necessary multimodality treatment results in disfigurement, severe speech, swallowing, and breathing problems and substantial healthcare costs. Since early detection of HNSCC could increase survival rates from 40% to 80%, a simple and inexpensive screening test would be useful. Currently physical exam, though inadequate, is the only screening tool available for this oppressive disease. Saliva provides an optimum medium for screening since it bathes the tumor and is convenient to obtain noninvasively. Several markers including solCD44, HA, and HAase have been identified in saliva and are overexpressed in HNSCC patients compared to controls. A panel of markers are described for the identification of early HNSCC with high sensitivity and specificity.

Definitions

The following terms are used as defined below throughout this application, unless otherwise indicated.

"Marker" or "biomarker" are used interchangeably herein, and in the context of the present invention refer to a polypeptide (of a particular apparent molecular weight, or, in the case of HA, a molecule made of repeating disaccharide units) which is differentially present in a sample taken from patients having head and neck squamous cell carcinoma (HNSCC) as compared to a comparable sample taken from control subjects (e.g., a person with a negative diagnosis, normal or healthy subject).

The phrase "differentially present" refers to differences in the quantity and/or the frequency of a marker present in a sample taken from patients having for example, head and neck squamous cell carcinoma (HNSCC) as compared to a control subject. For example, a marker can be a polypeptide which is present at an elevated level or at a decreased level in samples of patients with head and neck squamous cell carcinoma (HNSCC) compared to samples of control subjects. Alternatively, a marker can be a polypeptide which is detected at a higher frequency or at a lower frequency in samples of patients compared to samples of control subjects. A marker can be differentially present in terms of quantity, frequency or both.

A marker, compound, composition or substance is differentially present between the two samples if the amount of the marker, compound, composition or substance in one sample is statistically significantly different from the amount of the marker, compound, composition or substance in the other sample. For example, a compound is differentially present between the two samples if it is present at least about 120%, at least about 130%, at least about 150%, at least about 180%, at least about 200%, at least about 300%, at least about 500%, at least about 700%, at least about 900%, or at least about 1000% greater than it is present in the other sample, or if it is detectable in one sample and not detectable in the other.

Alternatively or additionally, a marker, compound, composition or substance is differentially present between the two sets of samples if the frequency of detecting the polypeptide in samples of patients' suffering from head and neck squamous cell carcinoma (HNSCC), is statistically significantly higher or lower than in the control samples. For example, a biomarker is differentially present between the two sets of samples if it is detected at least about 120%, at least about 130%, at least about 150%, at least about 180%, at least about 200%, at least about 300%, at least about 500%, at least about 700%, at least about 900%, or at least about 1000% more frequently or less frequently observed in one set of samples than the other set of samples. These exemplary values notwithstanding, it is expected that a skilled practitioner can determine cut-off points, etc. that represent a statistically significant difference to determine whether the marker is differentially present.

"Diagnostic" means identifying the presence or nature of a pathologic condition and includes identifying patients who are at risk of developing HSCC. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

The terms "detection", "detecting" and the like, may be used in the context of detecting biomarkers, or of detecting HNSCC (e.g. when positive assay results are obtained). In the latter context, "detecting" and "diagnosing" are considered synonymous.

A "test amount" of a marker refers to an amount of a marker present in a sample being tested. A test amount can be either in absolute amount (e.g., μg/ml) or a relative amount (e.g., relative intensity of signals).

A "diagnostic amount" of a marker refers to an amount of a marker in a subject's sample that is consistent with a diagnosis of head and neck squamous cell carcinoma (HNSCC). A diagnostic amount can be either in absolute amount (e.g., μg/ml) or a relative amount (e.g., relative intensity of signals).

A "control amount" of a marker can be any amount or a range of amount which is to be compared against a test amount of a marker. For example, a control amount of a marker can be the amount of a marker in a person without head and neck squamous cell carcinoma (HNSCC). A control amount can be either in absolute amount (e.g., μg/ml) or a relative amount (e.g., relative intensity of signals).

The terms "polypeptide," "peptide" and "protein" are used interchangeably herein to refer to a polymer of α-amino acid residues, in particular, of naturally-occurring α-amino acids. The terms apply to amino acid polymers in which one or more amino acid residue is an analog or mimetic of a corresponding naturally-occurring amino acid, as well as to naturally-occurring amino acid polymers. Polypeptides can be modified, e.g., by the addition of carbohydrate residues to form glycoproteins. The terms "polypeptide," "peptide" and "protein" include glycoproteins, as well as non-glycoproteins.

"Detectable moiety" or a "label" refers to a composition detectable by spectroscopic, photochemical, biochemical, immunochemical, or chemical means. For example, useful labels include $^{32}P$, $^{35}S$, fluorescent dyes, electron-dense reagents, enzymes (e.g., as commonly used in an ELISA), biotin-streptavidin, dioxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that can be used to quantify the amount of bound detectable moiety in a sample. Quantitation of the signal is achieved by, e.g., scintillation counting, densitometry, or flow cytometry.

"Antibody" refers to a polypeptide ligand substantially encoded by an immunoglobulin gene or immunoglobulin genes, or fragments thereof, which specifically binds and recognizes an epitope (e.g., an antigen). The recognized immunoglobulin genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well characterized fragments produced by digestion with various peptidases. This includes, e.g., Fab' and F(ab)'$_2$ fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. "Fc" portion of an antibody refers to that portion of an immunoglobulin heavy chain that comprises one or more heavy chain constant region domains, $CH_1$, $CH_2$ and $CH_3$, but does not include the heavy chain variable region.

By "binding assay" is meant a biochemical assay wherein the biomarkers are detected by binding to an agent, such as an antibody, through which the detection process is carried out. The detection process may involve radioactive or fluorescent labels, and the like. The assay may involve immobilization of the biomarker, or may take place in solution.

"Immunoassay" is an assay that uses an antibody to specifically bind an antigen (e.g., a marker). The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity).

The terms "subject", "patient" or "individual" generally refer to a human, although the methods of the invention are not necessarily limited to humans, and should be useful in other mammals.

"Sample" is used herein in its broadest sense. A sample comprising polynucleotides, polypeptides, peptides, antibodies fragments and derivatives thereof may comprise a bodily fluid; a soluble fraction of a cell preparation, or media in which cells were grown; a chromosome, an organelle, or membrane isolated or extracted from a cell; genomic DNA, RNA, or cDNA, polypeptides, or peptides in solution or bound to a substrate; a cell; a tissue; a tissue print; a fingerprint, skin or hair; fragments and derivatives thereof.

By "at risk of" is intended to mean at increased risk of, compared to a normal subject, or-compared to a control group, e.g. a patient population. Thus a subject "at risk of" developing HNSCC is at increased risk compared to a normal population, and a subject "at risk of" a recurrence of HNSCC may be considered at increased risk of having a recurrence as compared to the risk of a recurrence among all treated HNSCC patients "Increased risk" or "elevated risk" mean any statistically significant increase in the probability, e.g., that the subject will develop HNSCC, or a recurrence thereof. The risk is preferably increased by at least 10%, more preferably at least 20%, and even more preferably at least 50% over the control group with which the comparison is being made.

"CD44 marker" is intended to include soluble CD44 and isoforms thereof.

Head and Neck Squamous Cell Carcinoma (HNSCC) Biomarkers

In one embodiment, a method of detecting and diagnosing head and neck squamous cell carcinoma (HNSCC) comprises assaying for at least one biomarker in a subject sample, and correlating the detection of the biomarker(s) with a diagnosis of HNSCC or with increased risk of development of HNSCC, wherein the correlation takes into account the number of and level of biomarker(s) in the sample, as compared to normal values. In a preferred embodiment, the biomarker(s) is selected from HA, HAase, and CD44. For a diagnosis of HNSCC or increased risk thereof, at least one of the biomarkers is detected, more preferably, a plurality of the biomarkers are detected. Preferably, one or more isoforms of solCD44 is detected.

The subject sample may be selected, for example, from the group consisting of saliva, an oral rinse, blood, blood plasma, serum, urine, tissue, cells, and liver. Preferably, the sample is saliva or an oral rinse. Saliva can be collected using many methods. One common method is whole saliva collection. Saliva is collected, often over a set period of time, from the anterior oral cavity, where the majority is released under resting conditions. Oral rinses involve use of a set amount of a fluid, often saline, that is manipulated in the mouth and helps release substances adherent to the lining of the oral cavity, larynx and pharynx. It is theorized that whole saliva may reflect systemic expression of substances while oral rinses are more reflective of local expression of substances.

The CD44 marker is intended to include soluble CD44 and isoforms thereof.

The biomarkers can be detected using a protein assay, binding assay, an immunoassay, or any other suitable assay known to those of skill in the art. Exemplary assays are described in detail in the examples which follow. For a positive diagnosis of HNSCC or increased risk thereof, the biomarkers and/or total protein detected are elevated as compared to a normal healthy control.

In another embodiment, detection of at least one biomarker is diagnostic of tumor staging. It has been shown, for example, in bladder cancer that certain biomarkers are indicative of aggressive tumors (Lokeshwar et al., 2000, J. Urol. 163:348-56), and it is expected that the presence/amount of the biomarkers disclosed herein will be indicative of tumor staging in HNSCC.

Saliva as a screening medium: Saliva is becoming a well-accepted screening medium for various disease processes. It has an advantage over blood because it is readily accessible and noninvasive. The average daily production of whole saliva varies between 1 and 1.5 liters. Components of whole saliva include blood and blood derivatives from intraoral bleeding and gingival crevicular fluid, extrinsic substances such as food, epithelial lining cells, microbes, bronchial, nasal, salivary gland secretions. The majority of saliva, in the unstimulated state, originates from submandibular glands (65%) with 20% from the parotid gland and the remainder from sublingual and minor salivary glands located throughout the upper aerodigestive tract (UADT). Ninety-nine percent water, saliva contains a variety of electrolytes, immunoglobulins, proteins, enzymes, mucins, and nitrogenous products and is hypotonic especially in the unstimulated state. Normal pH ranges from 6-7. The salivary flow rate is influenced by the size of the salivary glands, hydration status, nutritional state, stimulus, and gender. Total protein concentrations of whole saliva in the unstimulated state give an accurate indication of the hydration state of an individual. Saliva is typically assayed as the product of an oral rinse, as described, for example, below.

CD44 comprises a family of isoforms expressed in many cell types. These isoforms arise from alternative splicing of a region of variable exons (exons 5-14) present in CD44 mRNA. They differ in primary amino acid sequence as well as in amount of N- and O-glycosylation. Isoforms are found in normal cells as CD44 standard (CD44s), CD44 epithelial (CD44E) or CD44v8-10, and CD44v3-10 in keratinocytes. Other CD44 variant isoforms (CD44v) are differentially expressed in some tumors. CD44 mediates a direct link between the extracellular matrix and the cytoskeleton via their conserved extracellular HA binding regions and intracellular ankyrin binding regions. CD44 proteins are also released in soluble form (solCD44) via proteases and are detectable in normal circulation and saliva. Detection methods using solCD44 are described, e.g., in U.S. application Ser. No. 11/090,705, filed Mar. 28, 2005, which is incorporated herein by reference.

Overexpression of normally expressed isoforms also promotes oncogenesis. CD44 transfection increases migration and confers metastatic potential to some cell types, while blocking cell surface CD44 binding to HA reduces tumor cell growth and migration. CD44 associates with other molecules to mediate oncogenic signaling. These include members of the ERBB family of receptor tyrosine kinases such as ERBB 1 and ERBB2. CD44 also functions as a platform for growth factors and members of the matrix metalloproteinase (MMP) family of enzymes, further contributing to signaling events. One member of the MMP family, membrane-type 1 MMP (MT1-MMP) cleaves CD44 to its soluble form. This cleavage results in increased cell migration. While MT1-MMP appears to be one of the main proteases involved in CD44 cleavage, there is evidence that others exist.

Hyaluronic Acid: HA is a nonsulfated glycosaminoglycan (GAG), overexpressed in certain cancers. HA is synthesized by hyaluronan synthase on the surface of cells and is comprised of repeating disaccharide units of D-glucuronic acid and N-acetyl-D-glucosamine. It is present in body fluids, tissues, and extracellular matrix. It interacts with cell surface receptors (e.g., CD44, RHAMM, etc.) and, through these interactions, regulates cell adhesion, migration, and proliferation. Depending upon the type of tumor, HA may be synthesized by stromal cells, tumor cells or both. In tumor tissues, HA supports metastasis by promoting tumor cell migration, offering protection against immune surveillance and causing a partial loss of contact-medicated inhibition of cell growth and migration. Small fragments of HA are angiogenic and have been isolated from urine of bladder cancer patients, prostate cancer tissue, and saliva from HNSCC patients. Concentrations of HA are elevated in several cancers, including colon, breast, prostate, bladder and lung. Tissue expression of HA in tumors such as colon and breast, indicates a poor prognosis.

Hyaluronidase: HAase is an endoglycosidase that degrades HA into small angiogenic HA fragments. HA and HA fragments stimulate endothelial cell proliferation, adhesion and migration by activating the focal adhesion kinase and MAP kinase pathways. HAase alters the expression of CD44 isoforms and is associated with increased tumor cell cycling. Of the 6 human HAases encoded by different genes, three are characterized at the protein level.

Kits

The assays of the present invention are ideally suited for the preparation of kits. Such a kit may comprise a carrier means being compartmentalized to receive in close confinement there with one or more container means such as vials, tubes and the like, each of said container means comprising the separate elements of the immunoassay. For example, there may be a container means containing a first antibody immobilized on a solid phase support, and a further container means containing a second detectably labeled antibody in solution. Further container means may contain standard solutions comprising serial dilutions of the HNSCC biomarkers to be detected, or appropriate quantities of the biomarkers in dry or concentrated form to be made up into standard solutions by the end user. The standard solutions of HNSCC biomarkers may be used to prepare standard curves with the concentration of each HNSCC biomarker plotted on the abscissa and the detection signal on the ordinate. The results obtained from a sample containing any one of the HNSCC biomarkers may be interpolated from such a plot to give the concentration of each detected biomarker.

In one embodiment, a kit for diagnosing HNSCC or elevated risk thereof in a subject comprising a panel of biomarkers is provided, the kit comprising (a) a substrate for holding a biological sample isolated from a human subject suspected of having HNSCC or of having elevated risk thereof, (b) one or more fluorogenic agents that detect biomarkers; (c) a panel of biomarkers; and, (d) printed instructions for reacting the agent with the biological sample or a portion of the biological sample to detect the presence or amount of at least one marker in the biological sample. Preferably, the kit comprises a panel of biomarkers of any one or more of hyaluronic acid (HA); hyaluronidase; and CD44. Optionally, the kit further comprises antibodies specific for any one or more biomarkers: HA, HAase, and CD44, and means for determining total protein. For a positive diagnosis based on the results of using the kit, at least one biomarker in a patient is elevated as compared to a normal healthy control.

The kit can provide both a panel of HNSCC biomarkers, e.g. to be used for standard curves, and antibodies thereto if desired. The kit will detect biomarkers using antibodies or other suitable detection methods.

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention become apparent to those skilled in the art upon review of the specification. The scope of the invention should, therefore, be determined not with reference to the above description, but instead should be determined with reference to the appended claims along with their full scope of equivalents.

This application claims priority to U.S. provisional application No. 60/799,925, filed May 12, 2006, the entire contents of which are incorporated herein by reference. All publications and patent documents cited in this application are incorporated by reference in pertinent part for all purposes to the same extent as if each individual publication or patent document were so individually denoted. By their citation of various references in this document, Applicants do not admit any particular reference is "prior art" to their invention.

EXAMPLES

Example 1

Detection of HA, HAase, CD44 and Interleukin-8 (IL-8)

solCD44 appears to be a robust marker for HNSCC. In an effort to increase sensitivity and specificity for detecting HNSCC, a panel of markers was examined, to attempt to improve those parameters. Twelve HNSCC saliva specimens and 12 matched control saliva specimens were studied. HNSCC samples were taken in consecutive order from a randomly generated database. Subjects were excluded if they had a limited ability to gargle. There were no significant differences between the HNSCC and control groups with regard to gender, age, race, ethnicity, smoking history, alcohol consumption or oral health. HNSCC subjects were taken in consecutive order from a randomly generated database. Controls were selected to match subjects with respect to gender, age, race ethnicity, smoking alcohol and oral health. HNSCC patients were stages 1-3.

HA concentration was measured using the ELISA-like assay described by Fosang et al (*Matrix*. 1990;10: 306-13) and modified by Lokeshwar et al (*Cancer Res.* 1997; 57: 773-77). Using the competitive binding principle, serial duplicate dilutions of saliva of cell lines were incubated in HA-coated microtiter plates with biotinylated HA binding protein. Plates were washed, HA binding protein was quantitated with an avidin-biotin detection system, and HA concentration was determined via standard graph. HAase levels were measured using an ELISA-like assay similar to that by Stern and Stern (*Matrix* 1992; 12: 397-03) with modifications by Lokeshwar et al (*Cancer Res.* 1997; 57: 778-83). Microtiter wells coated with HA were incubated with duplicate serial dilutions of saliva for 16 hours in assay buffer. HA remaining on the wells was determined using the same biotinylated HA-binding protein and avidin-biotin detection system as the HA test. HAase concentration was determined via standard graph. For the IL-8 test, samples were run in triplicate and the test performed according to the manufacturers instructions. After determining average marker levels for each sample, the optimal sensitivity, specificity and accuracy was calculated for each marker. Then sensitivity, specificity and accuracy were evaluated for combinations of markers.

TABLE 1

Sensitivity, specificity and accuracy of tumor marker panel:

|  | CD44 | HA | HAase | IL-8 | CD44 + H + HAase | CD44 + HA + HAase + IL-8 |
|---|---|---|---|---|---|---|
| Sensitivity | 75% | 50% | 42% | 50% | 92% | 92% |
| Specificity | 83% | 835 | 83% | 83% | 75% | 67% |
| Accuracy | 79% | 67% | 63% | 67% | 83% | 79% |

In this study, the combination of CD44, HA and HAase resulted in the highest accuracy. Addition of IL-8 decreased the specificity resulting in decreased accuracy.

TABLE 2

| Marker | Average % CV |
|---|---|
| CD44 | 4.5 |
| HA | 6.0 |
| HAase | 9.0 |
| IL-8 | 1.32 |

For each marker, all specimens were tested in replicate on the same plate with resulting average % CV shown in Table 2.

Freeze-thaw cycles and stability: For each marker, 3-5 samples were aliquoted to determine whether significant changes in marker levels occur with multiple freeze-thaw cycles or after storage for 8 hours on ice. Our results show that all three markers are stable after multiple freeze-thaw cycles and storage on ice for 8 hours.

TABLE 3

| Marker | Freeze-thaw % CV | Ice vs −80° C. % CV |
|---|---|---|
| CD44 | 10.2 | 8.6 |
| HA | 14.3 | 2.4 |
| HAase | 11.1 | 5.7 |
| IL-8 | 5.8 | 16.3 |

Our previous work shows that CD44 is a robust marker for HNSCC, however, a panel of markers may improve specificity and sensitivity of HNSCC screening. We have previously shown that HA and HAase are elevated in saliva of HNSCC patients compared to controls. In our study of 12 HNSCC patients and 12 controls matched for tobacco and alcohol use, dental health, age, gender and race, the combination of solCD44, HA and HAase, detected 11/12 tumors whereas CD44 alone detected 9/12 tumors.

Collection of oral rinse: Samples are collected from patients at the clinic or screening site. For collection, five milliliters of normal saline is placed in the subject's mouths. Patients are asked to, swish for five seconds, gargle for five seconds and then spit into a specimen cup. Saliva is placed on ice for transport and stored at −80 degrees. As recommended, subjects are asked to refrain from oral hygiene procedures, smoking, eating and drinking for at least 1 hour prior to collection. Samples are stored on ice for transport since solCD44, HA and HAase levels are stable on ice for 8 hours prior to freezing at −80° C. The samples may be fractioned to permit multiple investigations without freeze-thaw cycles and stored at −80° C. Though neither fractioning nor successive freeze-thaw cycles have a significant effect on solCD44, HA or HAase levels, freeze-thaw cycles are avoided so that the samples can be used for future analysis of other tumor markers.

It is important that saliva samples that are obtained, have had contact with all mucosal surfaces of interest. HNSCC patients with large tumors, significant pain or tracheotomy tubes may have difficulty gargling, which may contribute to an increased false negative rate. To control for this, normal controls and HNSCC patient's gargles may be graded on a scale from 0 to 2, with "2" being an effective gargle. One is a weak gargle, and zero is inability to gargle. These data can also be analyzed to determine if poor gargling is associated with lower levels of markers in tumor patients and normals.

SolCD44, HA and HAase assays: The solCD44 ELISA is carried out according to the instructions supplied by the manufacturer (Bender MedSystems, Vienna, Austria) with modifications. This assay recognizes all CD44 normal and variant isoforms. Samples may be tested in batches of approximately 30 samples per plate and measured at full concentration. For the rare sample whose level exceeds that of the highest standard, a repeat measurement is made at ½ concentration. The HA and HAase tests are performed as described. Samples may be tested in batches of approximately 10 per plate at various concentrations to ensure that that the measured levels fall on the standard curve. A separate aliquot of saliva for each of the 3 assays; solCD44, HA and HAase can be prepared. To minimize error introduced by plate-to-plate variation, it is advisable that all assays be performed in duplicate on two separate plates, with results of the two plates averaged.

Quality Control: Since quality control is an ongoing process, full quality control measures for each test (CD44, HA and HAase) should be applied, with reproducibility between duplicates on the same plate and duplicates on separate plates being assessed. Further, two analysts can test the same 30 samples on the same day and the same analysts assess the same 30 samples on separate days to quantitate variation introduced by different analysts, and day-to-day variation. To account for day-to-day, batch-to-batch and performer-to-performer differences, the following daily consistency testing as recommended by the EORTC-NCI working group may be used. For each marker a calibration curve in duplicate, a precision profile, and run a high and low concentration control sample on each plate will be performed. Stability of the control samples by analyzing plots of absorbance versus dilution factor over time should be verified.

Comparing levels of solCD44, HA and HAase between HNSCC patients and controls: Preferably, cancer patients and control subjects should be characterized by demographic data (e.g., age, gender, race, and socioeconomic status) and risk factors such as tobacco and alcohol use and oral health. The characteristics of the two groups can be compared by Student's t-test for continuous variables and Chi-square test or Fisher's exact test for categorical data. The mean level for each marker can be calculated separately for HNSCC patients and control subjects (with and without benign disease), with corresponding confidence limits, and compared with Student's t-test. Subjects with benign disease may also be analyzed separately using the same methods, to determine if any marker is elevated with benign disease. Multiple regression will determine whether there is a significantly higher expression of each marker in HNSCC after adjusting for risk factors.

Selecting the best combination of markers for HN screening: In order to determine the combination of biomarkers yielding the highest sensitivity and specificity for detecting HNSCC cancer, the methodology of Li, et al can be followed (*Clip Cancer Res* 2004;10:8442-50). Briefly, receiver operator characteristic (ROC) curve analysis are performed for each biomarker to evaluate the predictive power of each. The optimal cutpoint for each biomarker is determined by selecting the marker-specific cutpoint that yields the maximum sensitivity and specificity. Area under the curve (AUC) is computed for each biomarker, and the one with the largest AUC will be selected as the biomarker having the highest predictive power for detecting HNSCC cancer. Next, using logistic regression, multivariate classification models can be constructed to determine the best combination of biomarkers for cancer prediction. With logistic regression the association of each biomarker on the dependent variable (cancer/non-cancer) singly and in combination while controlling for potential covariates, such as age, gender, and smoking history is calculated. Backward stepwise regression will be used to find the best final model. Leave-one-out cross-validation can be used to validate the final logistic regression model. A final ROC curve can then be computed from the final logistic model using the fitted probabilities from the model as possible cutpoints for computation of sensitivity and specificity. Finally, cluster analysis can be used to produce a classification tree for the entire group (cancers and controls) using the validated biomarkers as predictors (reference for cluster analysis).

Statistical Analysis: Variance in duplicate measures (analytical variability) is obtained by squaring the difference in duplicates and dividing by 2. The mean value of these duplicate variances ($S_A^2$) can be determined. Then, using the formula to determine coefficient of variation, the square root of the mean variance divided by the overall mean marker level multiplied by 100 will give $CV_A$.

To estimate $CV_1$, the following formula can be used, where $S_1^2$ and $S_A^2$ correspond to mean biologic within subject variance and mean analytical variance, respectively.

$$S_1^2 + S_A^2/2 = \text{mean measured within subject variance}$$

Mean measured within subject variance is determined from the variance between samples collected two weeks apart. $CV_1$ is then determined using the formula for CV as above.

To estimate $CV_G$, the variance in the true means, $S_G^2$ is calculated using the following formula. Then $CV_G$ is calculated as previously discussed.

$$S_G^2 = [\text{Measured mean square between subject variance} - (S_A^2 + 2S_1^2)]/4$$

Once the values for $CV_A$, $CV_1$, and $CV_A$ are determined they can be incorporated into the following formulas to evaluate endpoints.

Evaluation of endpoints: The criteria to set performance standards was developed by Cotlove and is widely accepted (Fraser C G el at. *Critical Rev Clin Lab Sci* 1989;27:409-437). The criterion states that the maximum analytic variation should be less than or equal to half of the average within subject biologic variation. This is represented in the formula below where CV is coefficient of variation.

$$CV_A \leq \tfrac{1}{2} CV_1$$

Satisfaction of this criterion results in no more than a 12% increase in the measured over the true within subject variation. This will provide as with a measure to determine whether our analytic variability is sufficiently low.

Determining the significance in changes between serial measurements: The significance of changes in sequential results will be determined, using the index of heterogeneity as described by Fraser and Harris (*Critical Rev Clin Lab Sci* 1989; 27:409-437). If the heterogeneity is nonsignificant then the median of observed within subject variances will be used to determine a significant difference ($p \leq 0.05$) between samples using the formula below.

$$2.77(CV_A^2 + CV_1^2)^{1/2}$$

If the index of heterogeneity is significant then a distribution of true within subject variances can be developed and the upper percentile points used to calculate the critical difference.

For screening purposes, an individual marker level is determined as positive or negative based on a population based reference level. If the within-subject variation is small compared to the between-subject variation, a significant change in an individual marker level may not be perceived as significant when using population-based cut-off point. The following formula, which is an accepted index to determine whether individual values can be compared usefully with reference values, can be used:

$$(CV_1^2 + CV_A^2)^{1/2}/CV_G < 0.6$$

Harris has shown that if index levels are less that 0.6 the population-based reference value is usually insensitive to significant fluctuations in an individual subject. In this case the probability that an observed level will fall within the conventional normal range is greater than the specified probability that is derived from the distribution of the population as a whole (Harris E. K. *Clin Chem* 1974; 20:1535-42). When the reference values is insensitive to individual changes, following marker levels over time in an individual is usually more useful than comparing one set of marker levels to a reference level.

Three components of variation can be determined: the homogeneity of 1) variances in the 60 duplicate measures (analytic variability), 2) variances in the 60 repeat collections (within subject variability), and 3) mean marker level (between subject variability) for 30 subjects.

In order to determine outliers for the variances in each subject's replicate measures, and within subject variances, Cochran's test can be used to test the ratio of the maximum variance to the sum of the variances. To test for outliers in between subject variability, Reed's criterion can be used (Reed A H, Henry R J and Mason Va. *Clin Chem* 1971; 17:275-84). This criterion analyzes the difference between the extreme value and the next highest (or lowest value). The value is rejected if the difference exceeds one-third the range of all values. This criterion assumes that the true distribution of values for a given parameter are normal.

Example 2

The Salivary Soluble CD44 Test

Subject Characteristics: Seventy-three HNSCC patients, 54 patients with benign diseases of the upper aerodigestive tract (UADT) and history of tobacco and/or alcohol use, and 10 normal nonsmoking controls were studied according to the protocol approved by the Institutional Review Board. All HNSCC patients had biopsy proven newly diagnosed or recurrent squamous cell carcinoma. Included were all stages and sites except nasopharynx, since nasopharyngeal carcinoma tends to behave differently than squamous cell carcinoma in other sites. Four HNSCC patients had no primary site disease but either a recurrence in neck lymph nodes (n=3) or a newly diagnosed malignant neck lymph node (n=1). Patients with benign diseases of the upper aerodigestive tract (UADT) (from here on referred to as benign disease) were obtained from a general otolaryngology clinic. Most of these patients also had a history of tobacco or alcohol use. Non-smoking, normal subjects were volunteers from healthcare and research fields. All subjects completed a written consent prior to enrollment Saliva Collection: Five milliliters of normal saline was placed in the subject's mouths. Patients were asked to swish for five seconds, gargle for five seconds and then spit into a specimen cup. Saliva was placed on ice for transport and stored at −80 degrees.

SolCD44 ELISA: Levels of solCD44s using an ELISA assay (Bender MedSystems, Vienna, Austria) that recognizes all CD44 normal and variant isoforms were measured. This assay has been used extensively in serum and other body fluids and correlates with cancer progression in many tumors. Specificity of the CD44 antibody is described in detail in the Bender MedSystems Manual. They detected no cross reactivity between this test and TNF-$\alpha$, TNF-$\beta$, TNF-R, IFN-$\alpha$2c, INF-$\gamma$, IL-8 annexin, sELAM-1, sl-selectin, s1CAM1, or HER-2. The specificity of the antibody was confirmed by Western blot.

Figure 6:
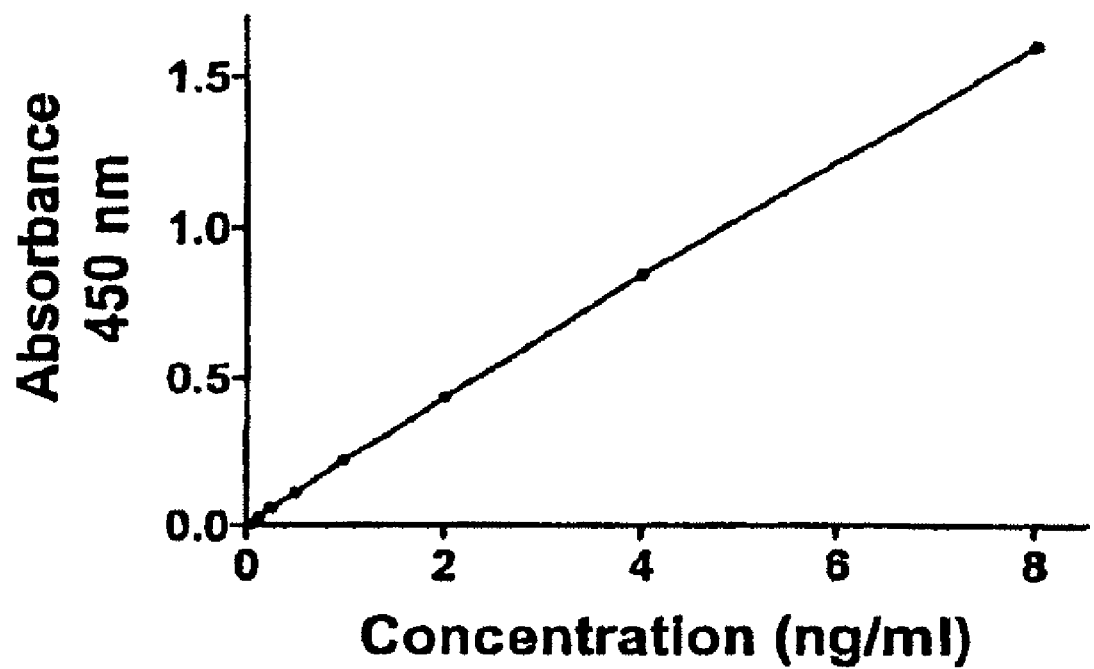
FIG. 6 is a graph showing a representative standard curve for solCD44 ELISA

The test involves a sandwich-type ELISA where a monoclonal anti-solCD44 antibody, adsorbed onto microwells, binds CD44 in the sample. Horseradish peroxidase-conjugated monoclonal anti-solCD44 antibody binds the CD44-antibody complex and reacts with a substrate solution to produce a colored product with an absorbance measured quantitatively at 450 nm. Sample concentrations are determined by a standard curve. We have modified the test: this ELISA plate is designed for use with plasma, serum and urine samples. Any matrix, i.e., serum, urine, saliva, may contain factors that affect ELISA test results; a matrix effect. Such effects are avoided by running the standards and samples in the same matrix. The standards are prepared in a synthetic saliva matrix (Salimetrics) diluted 1:5 in normal saline (since patients swish and gargle with 5 cc saline) and use a sample diluents (Sal metrics) developed for saliva samples. Samples were vortexed, centrifuged at 3,000 G and the supernatant was used for study. The test was performed at full, 1:2 and 1:4 dilutions. To adjust for hydration status, the solCD44 levels are normalized to protein using a protein assay (Bio-Rad). All sample assays were performed in triplicate. The protein and solCD44 concentrations for each sample were averaged and divided by the average protein concentration for that sample.

solCD44 ELISA Quality Control: The standard curve was generated using cubic spline curve fit. Standard curves were run in duplicate on each plate. Coefficient of determination ranged from 0.98-0.99 for all of the standard curves. A representative curve is shown in FIG. 6.

The precision of an assay is defined by the agreement between replicate measures. Samples (73 HNSCC and 54 control specimens) were repeated in triplicate at full concentration, 1:2 and 1:4 dilutions. The average coefficient of variation for the resulting 381 duplicate measurements was 4.5%.

Analytical sensitivity is defined as the lowest concentration detected that is significantly different than zero. Mean absorbance of our blanks run on 17 different plates was 0.02±0.015. Standard deviations were defined as significantly different and calculated the corresponding concentration from a representative standard curve. Using this method the analytical sensitivity of the test is 0.091 ng/ml.

Samples were run on a total of 17 ELISA plates. Since a reference standard is not available, the positive control sample containing 59 ng/ml of recombinant solCD44 was prepared in synthetic saliva diluted 1:5 in normal saline. This positive control was run in duplicate on each plate to assess differences between plates. Average coefficient of variation for duplicate readings of the positive control was 3.6%. Coefficient of variation between plates was 9.7%.

Statistical Analysis: Statistical analyses were performed using programs of the SAS Institute, Inc (Version 8.2). The mean solCD44 levels and protein levels were calculated separately for HNSCC patients, patients with benign disease, and nonsmoking controls, with corresponding confidence limits. Resulting means for HNSCC patients were compared with means for patients with benign disease and with nonsmoking normals using the Student's t-test. solCD44 and protein levels were compared between specific subgroups of cancer patients based on characteristics such as stage, site and tumor size. The four patients without disease at the primary site were excluded from this analysis. Student's Nest was used in most cases as only two groups were compared. ANOVA was used in cases where more than 2 groups were compared.

A good screening test for HNSCC must have high sensitivity and specificity. Using results from 73 HNSCC patients and 64 subjects without HNSCC the sensitivity and specificity of the solCD44 test was calculated at several cut-off points, thereby deriving its receiver-operator characteristic (ROC) curve.

Since HNSCC is tightly linked to risk factors such as tobacco and alcohol, such factors were controlled for. Patients most recently accrued, completed a questionnaire containing information on potentially important covariates including tobacco and alcohol exposure, race, ethnicity, gender, and SES. In addition, they received a head and neck examination. The two groups were compared using a student's t-test. The distribution of potentially important covariates was compared between the two groups by Chi-square analysis. Adjustments were made for imbalances using multiple regression.

Figure 7:
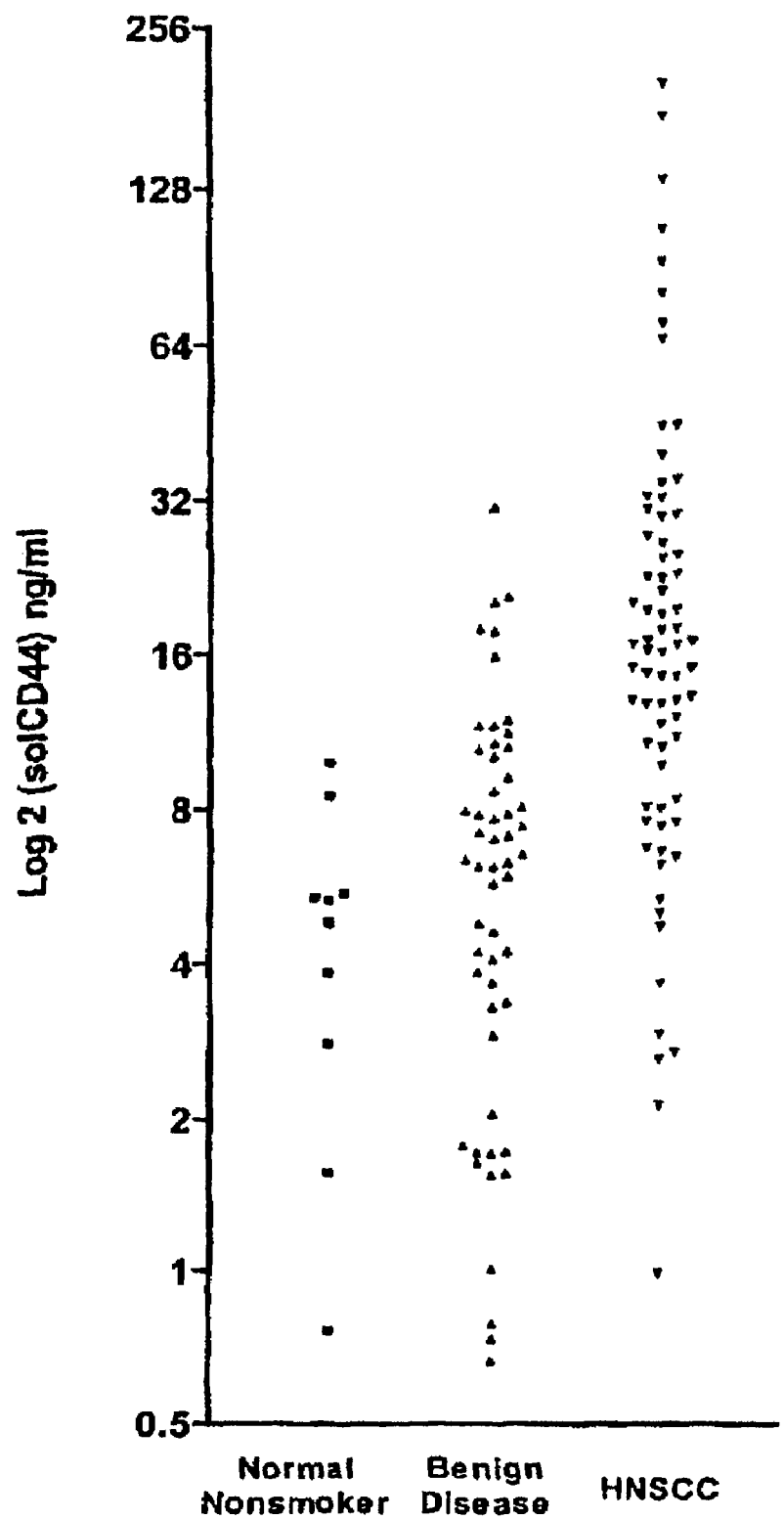
FIG. 7 is a graph showing salivary solCD44 levels are elevated in HNSCC patients compared to normal nonsmokers and patients with benign disease. Data was transformed to log 2 solCD44 level to aide visualization of differences. Differences between HNSCC patients and the two groups without cancer both were highly statistically significant p<0.0001.

Results:

SolCD44 Levels: Seventy-three HNSCC patients had disease of the oral cavity, oropharynx, larynx or hypoparynx. The mean solCD44 level was 27.3 ($\pm$) 36.2 ng/ml for HNSCC patients, 7.4±6.0 ng/ml for the patients with benign disease ($p<0.0001$), and 4.8±2.8 ng/ml ($p<0.0001$) for normal nonsmokers. Results are shown in FIG. 7. Four of the HNSCC patients with cervical lymph node disease had no identified mucosal primary. One of the four had newly diagnosed disease and the other three had recurrences to neck lymph nodes. All 4 of these patients had significantly elevated mean salivary solCD44 levels compared to the control groups (22.0 ng/ml, $p<0.05$) suggesting that the salivary solCD44 test is associated with HNSCC disease even when there is no evidence for disease on examination of the upper aerodigestive tract (UADT).

Levels were higher in patients with oral cavity and oropharynx tumors compared to larynx and hypopharynx tumors ($p<0.01$). Levels of CD44 did not correlate significantly with tumor stage, tumor size, history of previous HNSCC (recurrence or second primary) or history of prior radiation (Table 1) in this sample, although a larger sample size may reveal a correlation.

Salivary protein levels and normalized solCD44: Since salivary protein levels correlate with hydration status, protein assays were performed as previously described to determine if correcting for hydration status would improve results. Mean protein levels were significantly higher in the 73 cancer patients (1.1±0.9 mg/ml, $p<0.0001$) compared to patients with benign disease (0.5±0.3 mg/ml) and normal nonsmokers (0.6±0.4 mg/ml). It is possible that HNSCC patients were more dehydrated than normals due to swallowing difficulty. However, this is unlikely since small tumors do not usually cause swallowing difficulty and protein levels did not increase with increasing tumor size (Table 1). Since other proteins are elevated in saliva from HNSCC patients, it seems more likely that the increased protein concentration reflects elevated levels of many proteins.

Despite generally increased protein levels in HNSCC patients, the mean normalized solCD44 levels were significantly higher in the 73 HNSCC patients (32.0±49.6 ng/ml, p=0.05) compared to the benign disease group (18.7±14.7 ng/ml) and normal nonsmokers (8.3±3.2 ng/ml). Because protein levels were likely increased due to increased protein secretion into saliva in HNSCC cancer patients, solCD44 level alone appears to be the more reliable measurement. Further discussion will focus on the unnormalized solCD44 test.

Sensitivity and specificity of the solCD44 test for HNSCC: Using results from 73 HNSCC patients compared to the 64 patients without HNSCC, the sensitivity and specificity of the solCD44 test was calculated. A cut-off point set at 8.0 ng/ml resulted in a sensitivity of 78% and specificity of 70%, while a cut-off point of 12.0 ng/ml resulted in a sensitivity of 67% and specificity of 91%.

Since solCD44 levels were significantly elevated in patients with primary tumors in the oral cavity and pharynx compared to the larynx and hypopharynx we also calculated sensitivity and specificity for this subgroup compared to the 64 patients without HNSCC. For these 42 patients, a cutoff point of 8.0 ng/ml resulted in a sensitivity of 81% and a specificity of 70% while a cut-off point of 12.0 ng/ml resulted in a sensitivity of 74% and a specificity of 91%.

Since high specificity is important for a screening test, we analyzed data further using a cut-off point of 12 ng/ml. Using this cut-off point, there were 6 false positive results in the control group. These included 1 patient with adenoid hypertrophy, 2 patients with reflux laryngitis, 1 patient with obstructive sleep apnea (OSA), 1 patient with chronic laryngopharyngitis secondary to caustic ingestion, and 1 patient with two diagnoses, OSA and oral papilloma. Oral papilloma and caustic ingestion are infrequent diagnoses and did not occur in the true negative group. It may be argued that the patient with papilloma should be excluded from analysis since human papilloma virus is a known risk factor for HNSCC. For the other relatively common diagnoses distribution of benign disease of the UADT was relatively similar between the false positive group and true negative group.

With the cut-off point set at 12 ng/ml there were 24 false negative results. The solCD44 test correctly detected 73% of T1, 53% of T2, 80% of T3 and 60% of T4 disease. By stage the test correctly detected 67% of stage I, 54% of stage II, 82% of stage III and 67% of stage IV disease. The test also identified 67% of recurrences, 57% of second primaries, and 68% of newly diagnosed HNSCC. The solCD44 test detected 75% of oral cavity, 50% of laryngeal, 72% of oropharyngeal and 57% of hypopharyngeal primaries.

We have detailed information on potential confounding factors for 18 stage I-III newly diagnosed HNSCC and 48 benign disease patients. We further studied solCD44 expression in this group. The level of expression of solCD44 was also statistically significantly elevated in this cancer group compared to the benign disease group (23.9±31.3 ng/ml vs 7.0±5.9 ng/ml, p<0.05). The distribution of potentially important covariates was compared between the two groups by Chi-square analysis. The groups differed significantly with respect to several factors. Compared to the control patients, cancer patients were older, more likely male, less educated, reported less income, were more likely to have ever smoked cigarettes (>100 cigarettes in a lifetime), and were more likely to have poor oral health. Multiple regression analysis was used to adjust for these factors. Despite the imbalance in these characteristics, the level of expression of solCD44 remained statistically significantly elevated in this subset of cancer patients compared to controls after adjustment.

Soluble CD44 test: In our pilot study we showed that salivary solCD44 levels were elevated in HNSCC patients compared to normal controls. In this subsequent work, tobacco and alcohol use, gender, race, and SES are controlled for and evaluate the association of salivary solCD44 levels with common benign diseases of the UADT. One hundred and two HNSCC patients and 69 controls were enrolled from otolaryngology clinics at the University of Miami Hospitals and Clinics and Jackson Memorial Hospital. An additional 15 control patients were enrolled as normal volunteers. All subjects were enrolled according to the protocol approved by the Institutional Review Board. To ensure that controls included mainly smokers and drinkers (as is true of the HNSCC population), they were approached if they answered "yes" to tobacco or alcohol use on the clinic intake questionnaire. Control patients were excluded if they had a potentially malignant lesion or if final diagnosis of their condition was unknown. One control patient was excluded when, a severely dysplastic lesion was diagnosed in follow-up. All HNSCC patients had biopsy proven newly diagnosed or recurrent HNSCC. We included all stages and sites except nasopharynx, since nasopharyngeal carcinoma tends to behave differently than HNSCC in other sites. Subjects known to be pregnant or infected with human immunodeficiency virus were excluded.

TABLE 4

Means for Salivary SolCD44 Level

| | | N | Mean (ng/ml) | Std Dev | p value |
|---|---|---|---|---|---|
| Group | Benign/normal | 84 | 9.385 | 14.825 | <0.0001 |
| | Cancer | 97 | 24.714 | 32.747 | |
| Tumor Site | Larynx/Hypopharynx | 35 | 15.112 | 9.838 | 0.0057 |
| | Oral cavity/Oropharynx | 62 | 30.134 | 39.382 | |
| Tumor size | T1 | 27 | 26.005 | 29.109 | 0.3349 |
| | T2 | 28 | 19.359 | 18.693 | |
| | T3 | 19 | 35.952 | 56.550 | |
| | T4 | 23 | 20.433 | 21.584 | |
| Tumor Stage | I-II | 40 | 21.384 | 25.009 | 0.3726 |
| | III-IV | 57 | 27.050 | 37.272 | |
| Lymph node category | N0 | 65 | 20.450 | 23.849 | 0.1362 |
| | N1, N2, N3 | 32 | 33.374 | 45.066 | |

Results are summarized in Table 4 for 97 HNSCC with mucosal disease and 84 control patients. The mean salivary solCD44 level was 24.7 ng/ml for subjects with HNSCC and 9.4 ng/ml for the controls (p<0.0001). Levels tended to be higher in patients with oral cavity and oropharynx tumors compared to larynx and hypopharynx tumors. There was a tendency toward higher levels in patients with spread to the local lymph nodes compared to patients without nodal spread though this difference did not reach statistical significance. Levels did not correlate significantly with tumor size or stage, suggesting that the solCD44 test can detect HNSCC regardless of tumor size. Levels also did not correlate with history of previous HNSCC (recurrence or second primary) or history of prior radiation. Five HNSCC patients with cervical lymph node disease but no identified mucosal primary had elevated mean salivary solCD44 levels compared to the control group (19.2 ng/ml, p=0.15 t-test, p<0.01 nonparametric test) suggesting that the salivary solCD44 test is able to detect clinically occult mucosal disease.

Patients recently recruited, completed a questionnaire containing information on potentially important covariates including tobacco and alcohol exposure, race, ethnicity, gender, and SES. They also received an oral examination and assessment of their ability to gargle. This information is available for 43 newly diagnosed HNSCC patients and 63 controls. SolCD44 was also statistically significantly elevated in this cancer group compared to controls (20.4 ng/ml vs 10.2 ng/ml, p=0.017). The distribution of potentially important covariates was compared between the two groups by Chi-square analysis. Compared to the control patients, cancer patients were significantly older, more likely male, less educated, reported less income, used more tobacco products, and drank more alcohol. After controlling for risk factors significantly different between the two groups, the effect of group on the solCD44 level was still significant (p=0.0017). Therefore none of the risk factors is significantly associated with solCD44 level. We also evaluated whether oral health impacted solCD44 levels. From the questionnaire we determined that HNSCC patients had more teeth removed due to periodontal disease or decay than controls. Adjusting for this, the difference in solCD44 level between groups was still significant (p=0.0559). We also assessed HNSCC subjects and control subjects for ability to gargle. The two groups did not differ with respect to gargling ability.

Since salivary protein levels correlate with hydration status, protein assays were performed as previously described. However, protein levels were significantly higher in HNSCC patients (1.03 mg/ml, p<0.0001) compared to controls (0.565 mg/ml). Because of this, mean normalized solCD44 level between tumors (29.24 ng/ml p=0.087) and controls (20.05 ng/ml) did not reach statistical significance. Therefore, in a preferred embodiment, biomarkers are not normalized to protein levels when comparing tumor and control patients. Dehydration in the cancer patients (secondary to swallowing disturbance by the tumor) is one explanation for the difference in protein level between tumor and normal subjects. However, protein levels did not increase with increasing tumor size as would be expected if this occurred. Since other proteins are elevated in saliva from HNSCC patients, it seems more likely that the increased protein concentration reflects elevated levels of many proteins.

Using results from a group of 102 HNSCC patients and 84 controls, the sensitivity and specificity of the solCD44 test was calculated at several cutpoints, thereby deriving its receiver-operator characteristic (ROC) curve. A cutpoint set at 12 ng/ml resulted in a sensitivity of 62% and specificity of 89%. Our control group was designed to investigate patients at risk for development of HNSCC. It is encouraging that even with this, results are comparable to other widely used screening tests such as prostate specific antigen for prostate cancer (sensitivity 60-80%, specificity 90%) and the Papanicolaou test for cervical cancer (sensitivity 30-87%, specificity 86-100%). If we compare our HNSCC group to our normal volunteer group of 15 patients a cut-off point at 10 ng/ml yields a sensitivity of 70% and specificity of 93%.

We further investigated whether benign diseases of the upper respiratory tract were associated with high solCD44 levels. We divided the control group into 4 subgroups with an active benign disease process in the UADT and an additional subgroup without active disease of the UADT. These subgroups included patients with rhinitis/sinusitis (n=30, inflammation of the nasal passages or sinuses), obstructive sleep apnea (n=7, a sleep disturbance caused by upper airway obstruction often associated with enlarged tonsils), reflux (n=11, irritation of the UADT caused by regurgitated gastric contents) and other diseases of the UADT. The subgroup labeled "other disease" (n=21) included 4 patients with tonsillitis or pharyngitis with mean solCD44 level of 6.85 ng/ml. There were a total of 80 active diagnoses among 63 patients who completed questionnaires. Each subgroup was compared to the remaining control patients using a t-test. None of the subgroups had statistically significant elevations in solCD44 level. The obstructive sleep apnea group had significantly decreased levels (mean=4.303 p=0.0125). When we compared solCD44 levels in our 15 normal volunteers (mean=6.47 ng/ml) to this group of 63 patients with benign disease (mean=10.17 ng/ml) differences did not reach statistical significance using parametric (p=0.16 or nonparametric tests p=0.22).

TABLE 5

SolCD44 levels in dysplasia and carcinoma in situ (CIS)

| # | ng/ml | Site | Presentation at time of collection | Degree of dysplasia | Treatment of dysplasia | Follow-up (months) |
|---|---|---|---|---|---|---|
| 1 | 4.4 | Larynx | leukoplakia | CIS | Removal | No progression, (>48 months) |
| 2 | 88.3 | Oral cavity | History of HNSCC, new lesion with invasive carcinoma versus CIS on biopsy prior to collection | Only dysplasia on final pathology after removal | Wide excision | No progression (18 months) |
| 3 | 3.0 | Larynx | Leukoplakia | CIS | Removal | Dysplastic changes on repeat biopsy, further changes consistent with CIS on 3rd biopsy (17 mo) |
| 4 | 10.4 | Larynx | History of CIS, presents with leukoplakia | Mild-moderate dysplasia | Removal | No progression (14 mo) |
| 5 | 32.5 | Larynx | Carcinoma in situ diagnosed and removed shortly before collection | Repeat biopsy - no dysplasia | Not applicable | Developed leukoplakia of oropharynx 3 months post collection that resolved, then developed two invasive cancers in the larynx and hypopharynx (24 months) |
| 6 | 20.8 | Oropharynx | No disease, developed severe dysplasia 2.5 years post collection | Not available | Removal | Recurrent mild dysplasia on soft palate |

We performed the solCD44 test as described above on 6 patients with biopsy-confirmed dysplasia. SolCD44 levels were elevated in 50% of cases. The most significant finding is illustrated by patient 6 where solCD44 levels were high and the subject underwent disease progression. Patient 1 is interesting because this patient had low solCD44 levels and never progressed after 4 years follow-up, supporting a conclusion that solCD44 level distinguishes individuals who are likely to progress from those unlikely to progress.

Example 3

Cell lines: We obtained SCC-25 (oral HNSCC) from the American Type Culture Collection. UM-SCC-9 (tonsil SCC) and UM-SCC 11B (hypopharynx SCC) were gifts from Dr. TE Carey, University of Michigan. SCC-25 was grown in RPMI medium. UMSCC-9 and UMSCC-11B were grown in DMEM medium. All cell line media were supplemented with 10% fetal bovine serum, streptomycin and penicillin. At approximately 60% confluence, cultures were washed and incubated in serum free media supplemented with insulin, transferrin and selenium. These conditioned media (CM) were collected at 48-72 hours.

Western blots: Western blot analysis was performed on HNSCC cell lines UMSCC-11B, UMSCC-9, SCC-25 wild-type and SCC-25 CD44s transfectants. We also examined 2 solCD44 false positive control salivas, 2 HNSCC salivas, and 2 true negative control saliva samples. Proteinase inhibitors were added prior to saliva storage to prevent post-collection degradation. All blots were performed using a standard western blot protocol. Samples were subjected to electrophoresis in a 10% SDS-polyacrylamide (Bio-Rad) 1mm gel under reducing conditions then proteins were transferred onto nitrocellulose blotting membranes (Pall Life Sciences) and blocked with 5% milk in TBS-Tween solution for 1 hour. The same primary antibody as the solCD44 ELISA capture antibody was used. A 1:1000 dilution was added to the 5% milk solution and the membranes incubated for 1 hour. After washing, a 1:10,000 dilution of the secondary antibody (anti-mouse IgG and biotin conjugate) in TBS-Tween was applied for 1 hour. The membrane was treated with streptavidin-biotinylated alkaline phosphatase complex followed by addition of color development solution (Bio-Rad).

The results are shown in FIG. 1. A set of bands around 75 kDA, a 65-70 kDa band, and a 50 kDa band are seen in all samples. The set of bands at 75 kDa likely corresponds to various glycosylation products of the membrane bound CD44s. The bands at 50 kDA and 65-70 kDa correspond to published fragments lengths for solCD44. These soluble forms appear to be the major components of CD44 in saliva. Additional bands are seen around 100 kDa, 130 kDa, and 200 kDa in both the HNSCC and positive control samples, suggesting the isoforms expressed in HNSCC and positive controls are the same. These results suggest that positive controls cannot be distinguished from HNSCC based on salivary solCD44 isoform expression. Actin staining suggests that some cell lysate is present in all of the samples and therefore may contribute to the CD44 levels detected by the solCD44 ELISA.

An oral HNSCC cell line, SCC-25, was transfected with the CD44 standard form (CD44s) to 1) determine if this is the major isoform in saliva specimens and 2) to verify that overexpression is associated with the process of tumorigenesis.

Preparation of CD44s construct: DNA from HNSCC cell lines was amplified by PCR using primers in CD44 exon 1 and exon 19. The PCR amplification product was cloned into the TOPO Vector (Invitrogen, pcDNA3.1/V5-His TOPO TA expression Kit) pcDNA3.1/V5-His. Following transformation, colonies were screened by PCR and grown. The construct was then purified by Miniprep (Qiagen) and confirmed by sequencing.

The purified CD44s construct was transfected into SCC-25 cells following the lipofectamine protocol provided by the manufacturer (Invitrogen). For transient transfection, cells were collected at 24 hour and analyzed for CD44 expression. For stable transfection, cells were-passaged into selective medium 1 day after the start of transfection. At 2 days the G148 antibiotic was added to select for expression of the transfected antibiotic-resistance gene. For this preliminary experiment, stably transfected cells were grown as a pool as described by Recillas-Targa rather than isolating individual clones. At the present time, we are isolating individual clones to confirm these results.

Figures 2A, 2B:
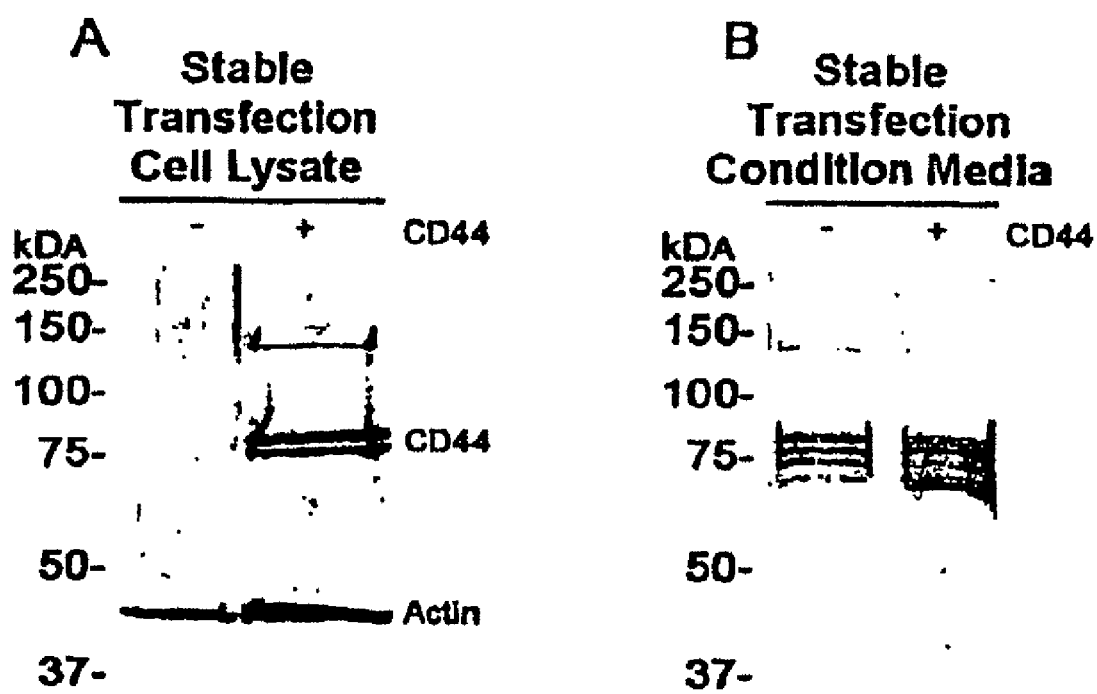
FIGS. 2A-2B are a scan of Western blots showing results following CD44s overexpression in SCC-25 transfectants versus wild-type.
Figure 3:
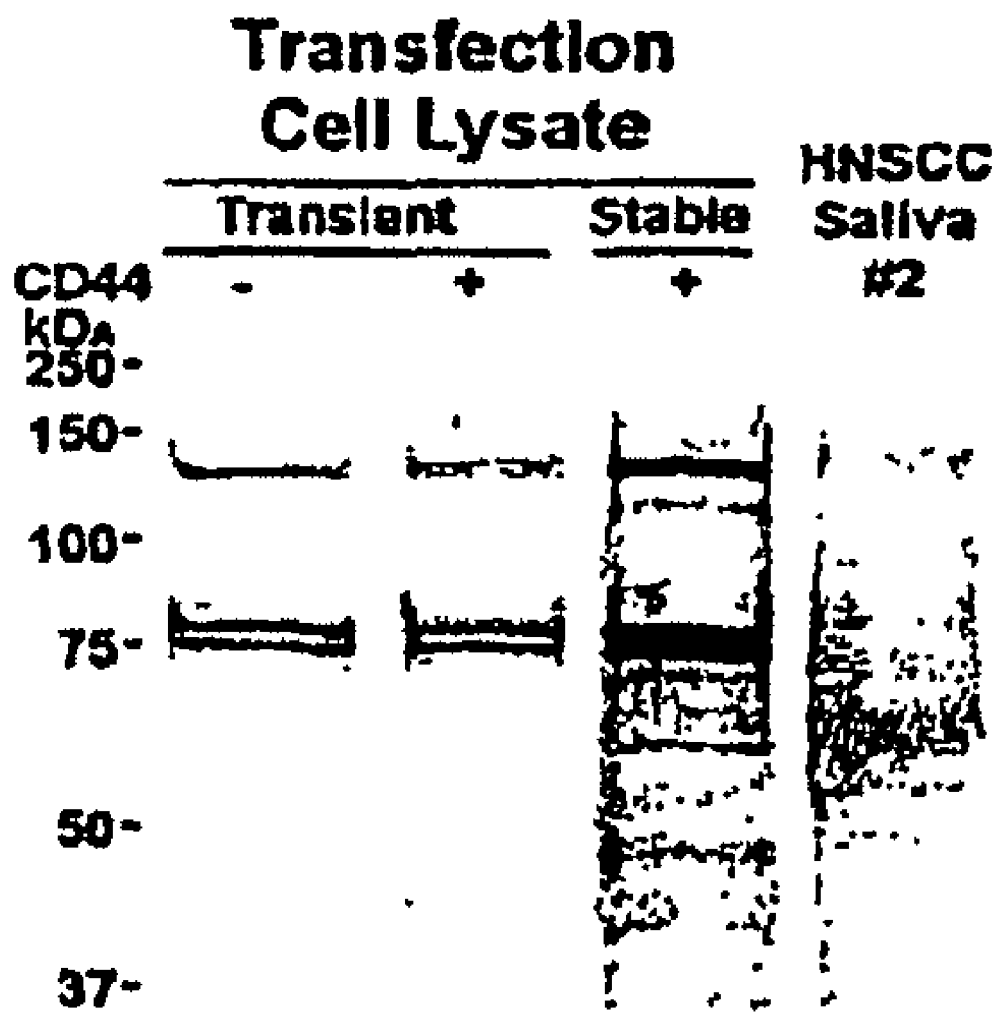
FIG. 3 is a scan of a Western blot showing expression of CD44 in SCC-25 cells following transient transfection with CD44s is identical to expression following stable transfection. To confirm that the CD44 expression pattern seen in the SCC-25 transfectant pool is a result of overexpression of CD44 and not an artifact of incorporation into the host genome, transient transfection of SCC-25 using CD44s was performed. The band at 130 kDa is also identical to the 130 kDa band seen in HNSCC saliva sample 2. ELISA confirmed that the transient transfectant contains 4 times more CD44 than the nontransfected cells.
Figure 4:
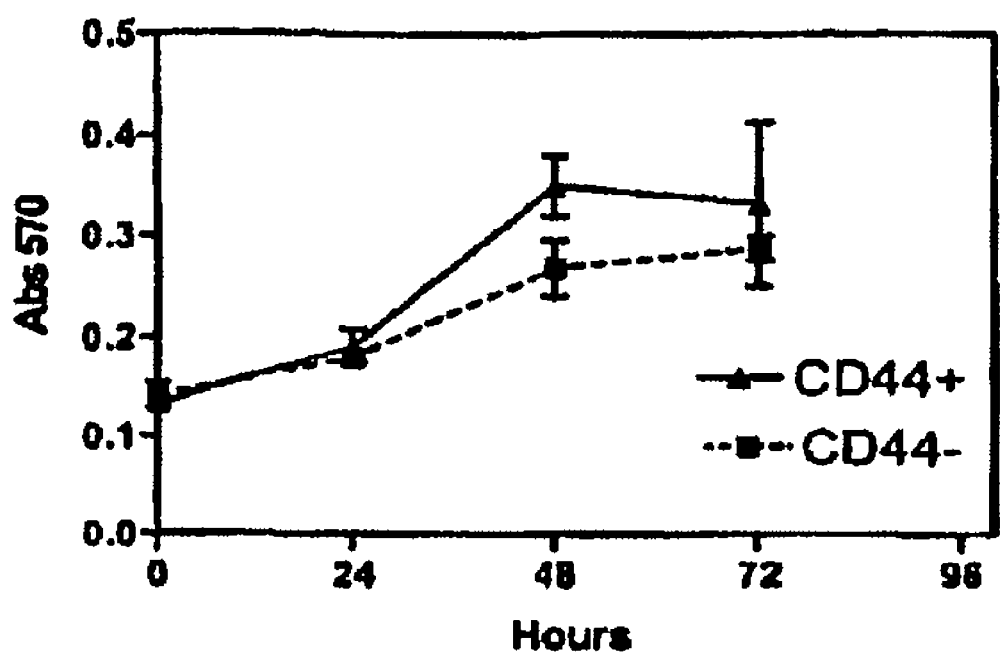
FIG. 4 is a graph showing overexpression of CD44s results in significantly increased cell growth. Differences in cell growth between CD44 transfectant (CD44$^+$) and the untransfected cells (CD44$^-$) is statistically significant at 48 hours (p=0.026). After 48 hours transfectant cells become confluent and begin to die.
Figure 5:
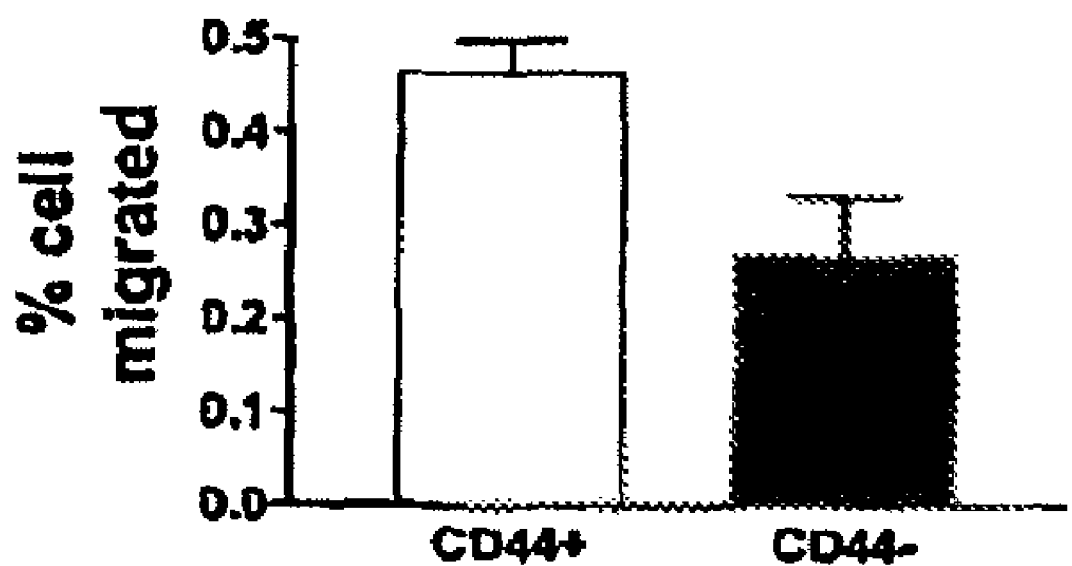
FIG. 5 is a graph showing overexpression of CD44s results in significantly increased cell migration. The difference in migration between transfectants and untransfected cells is statistically significant (p=0.01)

Results of the stable transfection are shown for the cell lysate (FIG. 2A) and conditioned media (FIG. 2B). Overexpression of CD44s results in increased expression of a doublet at 75 kDa in the cell lysate as well as a higher band around 130 kDa. Stronger expression of the 130 kDa band in the transfectant cell lysate raises the possibility that this is a variably glycosylated form of CD44s rather than an alternatively spliced isoform. In the CM, the doublet at 75 kDa may be from contamination by cell lysate rather than the soluble form of CD44, while the bands at 65-70 kDa and 50 kDa correspond to published solCD44 products (205). These bands are stronger in the CM from the transfectant compared to the untransfected cells. We confirmed overexpression of CD44 in both the cell lysate and CM using ELISA. We compared results normalized to protein to correct for potential variations in cell count between the groups. SCC-25 transfectants expressed 7.7 times more CD44 in the cell lysate and 2.8 times in the CM than untransfected cells.

To verify the link between CD44 and tumorigenesis in HNSCC, we performed migration and proliferation assays using the stable SCC-25 pool of transfectants compared to wild-type SCC-25 cells. Assays were performed in triplicate using the MTT assay according to previously published methods (Franzmann E. J. et al. *Otolaryngol Head Neck Surg* (2001)124:426-32; Bourguignong L. Y. W. et al., *J Biol Chem*. 2001 Mar. 9; 276(10):7327-36). Experiments were repeated 2-3 times under similar conditions and representative results are shown.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of diagnosing head and neck squamous cell carcinoma (HNSCC), or elevated risk of future occurrence thereof, in a subject, the method comprising:
    assaying a subject's sample comprising a bodily fluid for the presence of total protein and CD44;
    measuring the level of total protein and the level of CD44 in the subject's sample; and
    using the combination of total protein and CD44 levels in multivariate analysis to determine a combined score, whereby an increase in score above a cutpoint distinguishes subjects with HNSCC, or an elevated risk of future occurrence thereof, from subjects without HNSCC or at low risk of future occurrence thereof.

2. The method of claim 1, further comprising analyzing the subject's sample for the presence of and measuring the level of at least one of: hyaluronic acid (HA) and hyaluronidase (HAase), and using the level of at least one of: HA and HAse in multivariate analysis to determine a score, whereby an increase in score above a cutpoint distinguishes subjects with HNSCC, or an elevated risk of future occurrence thereof, from subjects without HNSCC or at low risk of future occurrence thereof.

3. The method of claim 2 wherein HA, HAase, total protein and CD44 are measured.

4. The method of claim 1, wherein the bodily fluid is selected from the group consisting of oral rinse, saliva, sputum, breath condensate, blood, blood plasma, serum, and urine.

5. The method of claim 1, wherein the subject's sample is saliva or an oral rinse.

6. The method of claim 1, wherein CD44 is soluble CD44 and isoforms thereof.

7. The method of claim 1, wherein the presence of total protein and CD44 is detected using a binding assay.

8. The method of claim 7 wherein the binding assay is an immunoassay.

9. A method of monitoring effectiveness of treatment of HNSCC in a subject comprising measuring the level of total protein and the level of CD44 in a biological sample obtained from said subject subsequent to receiving the treatment and combining these levels, and comparing the combined levels to combined total protein and CD44 levels detected prior to treatment in the same subject, wherein a decrease in combined levels of total protein and CD44 in the biological sample obtained from said subject subsequent to receiving the treatment compared to combined total protein and CD44 levels detected prior to treatment in the same subject, is indicative of effective treatment, and wherein the biological sample comprises a bodily fluid.

10. The method of claim 9 wherein HA, HAase, total protein and CD44 are measured.

11. A method for assessing HNSCC prognosis, comprising the steps of: (a) measuring the level of total protein and CD44 and at least one of hyaluronic acid (HA), and hyaluronidase (HAase) in a biological sample obtained from a subject after tumor treatment and using the combination of total protein and CD44 levels and at least one of HA and HAase in multivariate analysis to determine a combined score, (b) comparing the combined score of the biological sample to a combined score from a biological sample obtained before treatment, wherein a decrease in score from the biological sample obtained after tumor treatment and relative to the score from the biological sample obtained before treatment is indicative of successful treatment, positive prognosis, or both, and wherein the biological sample comprises a bodily fluid.

12. The method of claim 11, wherein HA, HAase, total protein and CD44 levels are measured.

13. The method of claim 11, wherein the biological sample is saliva or an oral rinse.

14. The method of claim 1, further comprising assessing the subject for at least one risk factor or demographic factor selected from the group consisting of: tobacco exposure, alcohol exposure, race, ethnicity, dental health, gender, level of education, and age.

15. The method of claim 14, wherein the assessment of the at least one risk factor or demographic factor combined with elevated levels of CD44 and total protein in the subject's sample compared to normal levels of CD44 and total protein in a control population correlates with a diagnosis of HNSCC.

16. A method of diagnosing HNSCC, or elevated risk of future occurrence thereof, in a subject, the method comprising:
assaying samples obtained from a subject over a period of time for the presence of total protein and CD44, wherein the samples comprise a bodily fluid;
measuring the level of total protein and the level of CD44 in the samples; and
using the combination of total protein and CD44 levels in multivariate analysis to determine a combined score, whereby an increase in combined score over time distinguishes subjects with HNSCC or elevated risk of future occurrence thereof, from subjects without HNSCC or at low risk of future occurrence thereof.

17. The method of claim 16, wherein the bodily fluid is selected from the group consisting of: oral rinse, saliva, sputum, breath condensate, blood, blood plasma, serum, and urine.

18. The method of claim 16, wherein the subject's samples are saliva or oral rinse.

19. The method of claim 16, wherein CD44 is soluble CD44 and isoforms thereof.

20. The method of claim 16, wherein the presence of total protein and CD44 is detected using a binding assay.

21. The method of claim 20 wherein the binding assay is an immunoassay.

22. The method of claim 9, wherein the bodily fluid is selected from the group consisting of oral rinse, saliva, sputum, breath condensate, blood, blood plasma, serum, and urine.

23. The method of claim 11, wherein the bodily fluid is selected from the group consisting of oral rinse, saliva, sputum, breath condensate, blood, blood plasma, serum, and urine.

* * * * *